(12) United States Patent
Foelling

(10) Patent No.: US 9,952,155 B2
(45) Date of Patent: Apr. 24, 2018

(54) METHOD AND APPARATUS FOR ILLUMINATION AND DETECTION IN RESOLFT MICROSCOPY

(71) Applicant: Leica Microsystems CMS GmbH, Wetzlar (DE)

(72) Inventor: Jonas Foelling, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 441 days.

(21) Appl. No.: 13/668,414

(22) Filed: Nov. 5, 2012

(65) Prior Publication Data

US 2013/0119273 A1    May 16, 2013

(30) Foreign Application Priority Data

Nov. 11, 2011    (DE) .................. 10 2011 086 230

(51) Int. Cl.
*G02B 21/06* (2006.01)
*G01N 21/64* (2006.01)
*G02B 21/16* (2006.01)

(52) U.S. Cl.
CPC ..... *G01N 21/6408* (2013.01); *G01N 21/6458* (2013.01); *G02B 21/06* (2013.01); *G02B 21/16* (2013.01)

(58) Field of Classification Search
CPC .............................. G02B 21/16; G02B 21/002
USPC .................... 250/458; 356/951, 952
See application file for complete search history.

(56) References Cited

U.S. PATENT DOCUMENTS

| 4,243,881 A  * | 1/1981  | Bethune ............... H01S 3/305 |
| | | 250/338.1 |
| 5,230,029 A  * | 7/1993  | Mendenhall ............ H01S 3/30 |
| | | 356/469 |
| 5,657,119 A  * | 8/1997  | Kawasaki ............ G01N 21/171 |
| | | 356/300 |
| 5,731,588 A  * | 3/1998  | Hell et al. ................ 250/458.1 |
| 6,816,256 B1 * | 11/2004 | Lloyd ............... G01N 21/6408 |
| | | 250/458.1 |
| 2001/0045529 A1* | 11/2001 | Iketaki ................. G01J 3/4406 |
| | | 250/493.1 |

(Continued)

FOREIGN PATENT DOCUMENTS

CN        101907766 A     12/2010
DE        4416558          8/1995

(Continued)

OTHER PUBLICATIONS

Hell (current opinion in the neurobiology 2004, 14:599-609, Concepts for nanoscale resolution and fluorescence microscopic).*

(Continued)

*Primary Examiner* — Casey Bryant
(74) *Attorney, Agent, or Firm* — Patentbar International, P.C.

(57) ABSTRACT

A method for illumination and detection in RESOLFT microscopy using a pulsed or continuous light source for excitation light and switching light is characterized in that the excitation light (4) is irradiated in pulses and in that the pulse of the excitation light (4) is longer than 150 picoseconds, preferably up to a few hundred picoseconds, and even up to a few nanoseconds. A corresponding apparatus uses the method according to the present invention.

13 Claims, 5 Drawing Sheets

(56) References Cited

U.S. PATENT DOCUMENTS

| | | | | |
|---|---|---|---|---|
| 2008/0088839 | A1* | 4/2008 | Hell | G01N 21/6458 356/318 |
| 2008/0192262 | A1* | 8/2008 | Enderlein | G01N 21/6458 356/610 |
| 2009/0242801 | A1* | 10/2009 | Engelhardt | G01N 21/6458 250/459.1 |
| 2010/0238438 | A1* | 9/2010 | Frankel | G01J 3/44 356/318 |
| 2012/0135459 | A1* | 5/2012 | Hell | A61K 49/0041 435/40.5 |
| 2012/0305803 | A1* | 12/2012 | Foelling | G01N 21/6458 250/459.1 |
| 2015/0001422 | A1* | 1/2015 | Englund | G01N 21/6458 250/459.1 |

FOREIGN PATENT DOCUMENTS

| | | | |
|---|---|---|---|
| DE | 10313138 B4 | 11/2007 | |
| EP | 0801759 B1 | 8/2001 | |
| FI | EP 0666473 A1 * | 8/1995 | ......... G01N 21/6408 |
| JP | H1195120 A | 4/1999 | |
| JP | 2001272344 A | 10/2001 | |
| JP | 2006227301 A | 8/2006 | |
| WO | 2006/016475 A1 | 2/2006 | |
| WO | 2011/065094 A1 | 6/2011 | |

OTHER PUBLICATIONS (Natural methods, vol. 8, #7, Jul. 2011, Sharper low—power STED manner be by time gating, npg).*

Stefan W. Hell, et al., Concepts for nanoscale resolution in fluorescence microscopy, Current Opinion in Neurobiology, 2004, pp. 599-609, No. 14, Elseveir.

Stefan W. Hell, Microscopy and its focal switch, Nature Methods, Special Features Perspective, Jan. 2009, pp. 24-32, vol. 6 No. 1, Nature America.

Stefan W. Hell, Jan Wichmann, Breaking the diffraction resolution limit by stimulated emission: stimulated-emission-depletion fluorescence microscopy, Optics Letters, Jun. 1, 1994, pp. 780-782, vol. 19, No. 11, Optical Society of America.

Thomas A. Klar, Stefan W. Hell, Subdiffraction resolution in far-field fluorescence microscopy, Optics Letters, Jul. 15, 1999, pp. 954-956, vol. 24, No. 14, Optical Society of America.

Stefan W. Hell, M. Kroug, Ground-state-depletion fluorescence microscopy: a concept for breaking the diffraction resolution limit, Applied Physics B: Lasers and Optics, 1995, pp. 495-497, vol. 60, Springer-Verlag.

Stefan Bretschneider, et al., Breaking the diffraction barrier in fluorescence microscopy by optical shelving, Physical Review Letters, May 25, 2007, p. 218103-(1-4), vol. 98, The American Physical Society.

D.H. Kim and J.U. Kang, Review: Upconversion microscopy for biological applications, Microscopy: Science, Technology, Applications and Education, 2010, pp. 571-582, A. Mendez-Villas and J. Diaz (Eds), FORMATEX.

Hell, S.W., Far-Field Optical Nanoscopy, Science, May 25, 2007, pp. 1153-1158, vol. 316, www.sceiencemag.org.

Hell, S.W., Far-Field Optical Nanoscopy, Single Molecule Spectroscopy in Chemistry, Physics and Biology, 2010, 19: pp. 365-396, Springer-Verlag.

Vicidomini, G., et. al., Sharper Low-power Sted nanoscopy by time gating, Nature Methods, Jul. 2011, vol. 8, No. 7, Nature America.

Moffitt, J R, et. al., Time-gating improves the spatial resolution of STED microscopy, Optics Express, Feb. 28, 2011, pp. 4242-4254, vol. 19, No. 5, OSA.

Schrof, Susanne et al, STED nanoscopy with mass-produced laser diodes, Optics Express, Apr. 25, 2011, pp. 8066-8072, vol. 19, No. 9.

* cited by examiner

METHOD AND APPARATUS FOR ILLUMINATION AND DETECTION IN RESOLFT MICROSCOPY

FIELD OF THE INVENTION

The present invention relates to a method for illumination and detection in RESOLFT microscopy using a pulsed or continuous light source for excitation light and switching light. The present invention also relates to an apparatus for carrying out the method of the present invention.

RESOLFT (REversible Saturable OpticaL (Fluorescence) Transitions) microscopy includes a group of light microscopic methods capable of producing particularly sharp images with high magnification. Despite the use of conventional objectives and diffracted beams, it is possible to achieve a resolution far beyond the diffraction limit down to the molecular scale (in this regard, see Stefan W. Hell, Marcus Dyba and Stefan Jakobs: Concepts for nanoscale resolution in fluorescence microscopy. Current Opinion in Neurobiology 2004, 14: pp. 599-609; Stefan W. Hell: Microscopy and its focal switch. Special Features Perspective, Vol. 6 No. 1, January 2009, Nature Methods.)

In conventional light microscopes, the capability of distinguishing between closely spaced features is about 200 nm. This is due to the wave nature of light. For example, in conventional light microscopes, the resolution limit is mainly determined by the wavelength of the light used and the numerical aperture. In RESOLFT microscopy, this limit is overcome. To this end, dyes are temporarily switched to a state in which they are unable to emit a (fluorescence) signal in response to illumination.

In accordance with the above explanations, RESOLFT microscopy is a variant of light microscopy which overcomes the diffraction limit. Thus, using RESOLFT microscopy, it is possible to detect and image features of a specimen which are actually too close together to be just resolved.

In RESOLFT microscopy, the principles of STED microscopy (see Stefan W. Hell, Jan Wichmann: Breaking the diffraction resolution limit by stimulated emission: stimulated-emission-depletion fluorescence microscopy. In: Optics Letters. 19, No. 11, 1994, pp. 780-782; Thomas A. Klar, Stefan W. Hell: Subdiffraction resolution in far-field fluorescence microscopy. In: Optics Letters. Vol. 24, No. 14, 1999, pp. 954-956.) and of GSD microscopy (see Volker Dose: Peer review. In: EPL, A Letters Journal Exploring the Frontiers of Physics. Vol. 89, 2009; Stefan W. Hell M. Kroug: Ground-state-depletion fluorescence microscopy: a concept for breaking the diffraction resolution limit. In: Applied Physics B: Lasers and Optics. Vol. 60, No. 5, 1995, pp. 495-497; Stefan Bretschneider, Christian Eggeling, Stefan W. Hell: Breaking the diffraction barrier in fluorescence microscopy by optical shelving. In: Physical Review Letters. Vol. 98, No. 5, 2007, p. 218103) are generalized to any kind of molecules that can be reversibly switched between two distinguishable states in the broadest sense. "Switching" of the dye molecules to at least one of two possible states can be achieved by the influence of light. In this connection, the term "switching" is to be understood in the broadest sense.

In RESOLT microscopy, the specimens to be examined are labeled with special molecules, usually fluorescent dyes. One uses optically driven, distinguishable states in the dye molecules. Specifically, the dye molecules are switched back and forth or up and down between at least two states. These states may be a signal-giving bright state and a non-signal-giving dark state. Switching of the dye molecules into at least one of the two states is achieved by the action of light The term "RESOLFT microscopy" is to be understood as a generic term under which different methods working according to similar principles are to be subsumed. STED (Stimulated Emission Depletion) microscopy, for example, belongs to RESOLFT microscopy. In that method, a fluorescent dye can change back and forth between an electronic ground state and an excited state and fluoresce in the process. In the dark state, the dye is permanently maintained in its ground state through stimulated emission. Thus, there are two configurations of fluorescent dyes, according to which the fluorescent dyes fluoresce in the signal-giving state, while in the dark state, no emission is perceptible.

Another method belonging to RESOLFT microscopy is GSD (Ground State Depletion) microscopy. Here, fluorescent dyes are used as markers. In the bright state, the dye can change back and forth between the ground state and the excited state and fluoresce in the process. For the dark state, the ground state of the molecule is depopulated. This means that the molecule is excited to a long-lived state from which no fluorescence occurs. As long as the molecule is in a long-lived dark state, it is not available in the ground state and, therefore, cannot be excited to fluoresce. Return to the bright state occurs spontaneously.

SPEM (Saturated Pattern Excitation Microscopy) and SSIM (Saturated Structured Illumination Microscopy) are also representatives RESOLFT microscopy. In these methods, initially negative images are produced and [then] mathematical image reconstruction is performed. The ground state takes the place of the dark state in accordance with the explanations given hereinabove. The first, excited state corresponds to the bright state.

Another method to be mentioned in the context of RESOLFT microscopy is upconversion microscopy (see D. H. Kim and J. U. Kang: Upconversion microscopy for biological applications, Microscopy: Science, Technology, Applications and Education, pp. 571-582). STAQ microscopy is also to be subsumed under RESOLFT.

It should be noted at this point that the present invention relates to a method and apparatus which may be used for illumination and detection in RESOLFT microscopy in general, regardless of the particular method used. What is important is the use of the basic principle of RESOLFT, the application of which relates to all conceivable representatives of this basic principle.

SUMMARY OF THE INVENTION

To simplify the explanation of the teaching of the present invention, the teaching, which relates to RESOLFT microscopy in general, will be described using the example of STED microscopy, which uses a pulsed or continuous light source for excitation light and stimulation light (corresponds to the switching light).

A corresponding apparatus of the aforementioned type is described in DE 44 16 558 C2, particularly with respect to scanning confocal fluorescence microscopy. In this apparatus, in order to increase the lateral resolution, a specimen point is illuminated with an excitation beam, as a result of which the fluorescent molecules acted upon by excitation light are converted to an excited state. Moreover, the specimen point is illuminated with a stimulation beam of suitable wavelength, as a result of which fluorescent molecules in the excited state can be returned to the ground state by the process of stimulated emission. The excitation beam and the stimulation beam (switching beam) are arranged in such a way that their intensity distributions or illumination patterns at least partially overlap one another in the object region. The fluorescent molecules lying in the overlap region are converted to the ground state by stimulated emission immediately after excitation by the excitation beam, so that only light from the fluorescent molecules is detected, the fluorescent molecules being located in the illumination pattern of the excitation beam but not in the illumination pattern of the stimulation beam, i.e. not in the overlap region of the illumination patterns of the illumination beam and the excitation beam.

The stimulated emission light and/or the reflected stimulation light can be filtered out of the detection beam path of the scanning microscope by means of optical filters, so that only fluorescent light from the region of the illumination pattern of the excitation beam, minus the overlap region of the two illumination patterns, is detected. This reduction allows the object region that contributes to the fluorescence emission to be reduced to below the limits of diffraction-limited imaging, and thus represents an improvement in resolution.

An apparatus for illumination and detection of an object in STED microscopy is already known from DE 103 13 138 B4, where the main beam splitter takes the form of a switchable beam splitter which, depending on the irradiated power of the stimulation light, can be switched to transmission when the excitation level in the region of the stimulation light distribution has become negligible. Here, one speaks very generally of gating.

In STED microscopy, as mentioned earlier, the sample is initially optically excited by an excitation beam of, for example, pulsed green laser light. Then, the so-called quenching is performed, namely by irradiation with stimulation light, so that stimulated emission of the sample occurs in a portion of the excited focal region at a wavelength that overlaps with the fluorescence spectrum of the excited dye. Typically, the stimulated emission is in a range between 700 and 800 nm. The regions outside the STED illumination emit in the "normal" fluorescence process.

STED microscopy is a technology which makes it possible to achieve a resolution beyond the classical diffraction limit, while in a typical microscope, the resolution is limited by the light's wavelength due to diffraction.

In a confocal microscope, the scanning laser spot cannot be smaller than a certain size, typically about 200 nm. Therefore, structures in the sample that are smaller than this value cannot be imaged.

In STED microscopy, in order to overcome the resolution limit in a confocal microscope, the scanning focused light distribution ("excitation light") used to excite the dyes in the object is superimposed with another light distribution, which is typically ring-shaped and has an intensity minimum at its center. The wavelength of this light distribution is selected to induce stimulated emissions ("STED light") from the dyes that are excited by the excitation light. In this way, it can be achieved that, of the area struck by the excitation light distribution, fluorescent light is, in practice, emitted only from the region in the center of the STED light distribution because this is where the STED light distribution has its minimum, and thus, does not cause stimulated emission. In all other regions illuminated by the excitation light, no fluorescent light is emitted because the fluorescence is instantly suppressed by immediate stimulated emission.

The light emitted through stimulated emission may be filtered out by appropriate filters, so that only the light from the center of the excitation light distribution will remain. The new effective light distribution obtained in this way is much smaller than the original one. This makes it possible to see much smaller structures in the sample.

With regard to the basic principle of STED microscopy, reference is also made to Hell, S. W., "Far-Field Optical Nanoscopy", Science, 316, 2007 and Hell, S. W., "Far-Field Optical Nanoscopy", Single Molecule Spectroscopy in Chemistry, Physics and Biology, Springer Verlag, 2010. The contents of these publications relating to STED microscopy are assumed to be known to those skilled in the art.

In STED microscopy, the temporal coordination of the excitation light and the stimulation light (STED-light) plays an important role.

A special variant of the STED method is the pulsed STED method. Here, the excitation light is irradiated toward the sample in a very short pulse of typically less than 150 picoseconds. Immediately thereafter, in a period much shorter than the typical lifetime of the excited state of a dye molecule, the stimulation light is irradiated, also in a pulse. This pulse is usually longer than the excitation light pulse and may have a pulse length of, for example, from a few hundred picoseconds to a few nanoseconds. The "lifetime" of an excited state is typically a few nanoseconds. The de-excitation and the emission of the associated photon are a stochastic process that has this average lifetime. Thus, if an assembly of molecules is illuminated by a short excitation pulse, it is possible to detect a fluorescence which decays exponentially, specifically with a characteristic decay constant of a few nanoseconds. Therefore, it is important to irradiate the stimulation light immediately after the fluorescence pulse because this is the only way to ensure that the fluorescence is suppressed to the extent possible by the STED light. If too much time were allowed to elapse, then not only photons from the center of the excitation light distribution, but also photons from other regions would be registered. These photons are undesirable, since they result in poor resolution.

It is also important that the excitation pulse be short in comparison to the lifetime of the excited state. If it were long, then the STED pulse would be too late for those molecules which are already excited at the beginning of the excitation pulse. Such molecules could then emit light before their fluorescent light is suppressed, and thus would contribute to poor resolution. It should also be noted that the STED pulse is usually several orders of magnitude more intense than the excitation pulse. Consequently, powerful lasers with high pulse energy are required.

Another known variant of the STED method is one in which continuous stimulation light is used (CW STED=Continuous Wave STED). Here, the stimulation light is not pulsed, but rather is continuously emitted for excitation. Accordingly, the stimulation light is irradiated continuously.

The STED method using continuous stimulation light has significant advantages in practice. For example, no consideration needs to be given to the critical time sequence of the pulses. In the case of pulsed stimulation light, the pulse spacing as well as the pulse lengths are extremely critical parameters. In particular, it is not easy to generate sufficiently short excitation pulses. Light sources capable of this are usually very expensive. Suitable pulsed light sources for the stimulation light are also expensive and there is only a limited number to choose from. This is different when CW lasers are used as a light source. A great choice of cost-effective, yet reliable CW laser sources which continuously emit light is available for both the excitation light sources and the STED light sources.

However, the CW STED method also has quite significant drawbacks. The resolution is far from being as good as in the pulsed STED method. This is because dyes may be excited at any time. The stimulation light, in turn, is not irradiated with maximum intensity in pulsed form immediately after excitation, but continuously. Therefore, a dye molecule which is excited at an instant t0 and has an extremely short excitation period "sees" little stimulation light, and therefore has little chance to be de-excited by stimulated emission. A dye molecule that has a longer lifetime "sees" more stimulation light and therefore is de-excited more effectively. Thus, although the CW STED method also contributes to improved resolution, the dye molecules mentioned first cause a deterioration in the resolution.

Since the excitation light is irradiated continuously, there is always a mixture of the two aforementioned cases. Consequently, the resolution is indeed increased, but not in an ideal way, and it is far from being optimal.

There is yet another STED method, which is known as "gated STED". In this regard, reference is made to Vicidomini, G., et. al., Nature Methods, 8(7), 2011 and Moffitt, J R, et. al., Optics Express, 19(5), 2011. The gated STED method is a combination of the two first-mentioned STED methods. While the excitation light is irradiated in short pulses, the stimulation light is irradiated continuously.

In order to prevent detection of "bad" photons; i.e., photons which are emitted shortly after the excitation pulse, all of these photons are rejected. This may be achieved, for example, by deactivating the detector for a short period of time or by not processing the signal of the detector during this period. By detecting only photons which are emitted after a certain time has elapsed after the excitation pulse, it can be ensured that these photons are actually the ones that are desired for analysis, namely those which come from the center of the excitation light distribution, where no stimulation light is irradiated at all, and which then contribute to high resolution. Thus, all other molecules, namely those outside the very center of the excitation light distribution have "seen" the STED light long enough, so that they very likely have been de-excited and do not emit photons.

In practice, the gated STED method has proven to be advantageous because it permits the use of relatively inexpensive and reliable CW lasers for generating the stimulation light. However, in this method, too, expensive short-pulse lasers must be used for the excitation light. This is a disadvantage, especially in view of the increasing cost pressure.

It is, therefore, an object of the present invention to provide both a method and an apparatus for illumination and detection in RESOLFT microscopy which will allow RESOLFT microscopy to be performed reliably with sufficiently high resolution. The cost should be kept as low as possible, especially with regard to the light sources needed.

The aforementioned object is achieved by the features of independent claims 1 and 12.

In accordance with the features of claim 1, the method of the present invention is characterized in that the excitation light is irradiated in pulses and in that the pulse of the excitation light is longer than 150 picoseconds, preferably up to a few hundred picoseconds, and even up to a few nanoseconds.

With regard to the apparatus according to the present invention, the object is achieved by the features of independent claim 12. In accordance with these features, the apparatus of the present invention is characterized in that a pulsed laser source is provided for irradiating the excitation light in pulses, the laser source being pulsed with a pulse duration of greater than 150 picoseconds, preferably up to a few hundred picoseconds, and even up to a few nanoseconds, in particular in the range from 400 picoseconds to 10 nanoseconds.

In accordance with the present invention, it has been discovered that it is possible in a sophisticated way to irradiate the excitation light in pulses and, in this connection, to keep the pulse of the excitation light within an advantageous time range; i.e., to define the pulse to be longer than 150 up to a few nanoseconds. This allows the use of inexpensive laser light sources.

Surprisingly, it has been found that, given a suitable implementation of the signal filter, there is no need to use short excitation pulses, which can only be generated by extremely expensive light sources. Quite to the contrary, such short excitation pulses are disadvantageous. Thus, it is suitable and particularly advantageous to irradiate pulses which are longer than usually short pulse lengths of less than 150 picoseconds, such as are commonly used in the prior art. The duration of the excitation pulse may advantageously be in the range from a few hundred picoseconds to a few nanoseconds. In particular, the length of the excitation pulses may correspond approximately to the lifetime (half-life) of the fluorescent state of a dye molecule in the sample that was excited to emission by the excitation light. Very surprisingly, this feature leads to an increased signal and also to improved resolution.

The difference in the pulse length of the excitation light, as implemented by the present invention, leads not only to an improved signal, but also to a significant technical simplification with respect to the excitation light sources. For example, pulse lengths in the range from a few nanoseconds to a few picoseconds can be implemented using inexpensive means, namely by suitable light sources which are much less expensive than light sources for pulse lengths of less than 150 picoseconds.

Moreover, according to the teaching of the present invention, the light intensity of the excitation pulses does not need to exhibit a sharply rising edge, as would be required for the short-pulse excitations known from the prior art. It is only the falling edge of the excitation pulse that should advantageously be reasonably steep. Accordingly, asymmetrical pulses are possible and adequate, which allows further technical simplification with respect to the light sources for generating the excitation light pulse.

This is because fast turning-off of the light; i.e., producing a sharply falling edge of the light pulse, can be achieved with simple means, such as, for example, by rapidly reversing the polarity of the power supply, whereas a steep rise in the light intensity is problematic in many lasers. According to the teaching of the present invention, there is no need for such a steep rise in the light intensity. This is another point that contributes to a cost reduction with respect to the light source.

It should be noted at this point that the present invention is suitable for both pulsed stimulation light sources (STED light sources) and CW stimulation light sources (CW STED light sources).

When the stimulation light (STED light) is irradiated in pulses, it is particularly advantageous that no stimulation light be delivered to the sample during the excitation light pulse. In this phase, all photons coming from the sample are rejected from detection and analysis. Upon or shortly after the activation of the stimulation pulse, the photons coming from the sample are detected and analyzed.

According to the teaching of the present invention, unlike the prior art, the excitation light is irradiated in a longer pulse which corresponds approximately to the half of the lifetime of the excited fluorescent state. Since the excitation light is light from a pulsed system, the stimulation light source is not active at this point in time; i.e., no stimulation light is irradiated. Unlike the prior art, all photons which are irradiated during the excitation period are rejected. They fall within the so-called "gating period". This is because these photons come from the entire excitation region, and not only from the center. It is only when the pulse of the stimulation light is active, or shortly after the activation of the stimulation light pulse, that the gating period is deactivated and photons can be detected. These photons are then very likely to come exclusively from the center of the excitation light distribution, as desired.

The method of the present invention has the advantage over the prior art that it allows the use of a long-pulse excitation light source which, because of its greatly simplified control electronics and the possibility of using very cost-effective laser sources, is simple and inexpensive to manufacture.

Another advantage over the prior art resides in the fact that the excitation period is longer and, therefore, more photons reach the detector. Since the excitation pulse may correspond approximately to the half of the lifetime of the excited state of the dye molecules, a significant number of molecules which are excited at the very beginning of the excitation pulse will emit after the end of the gating phase and be usable. A large number of usable photons are not emitted until after the end of the gating phase, so that they can also be detected. An even greater number of photons can be detected from molecules which are excited in the central portion of the excitation light. The photons which are emitted at the very end of the excitation pulse are also usable.

While in the prior art, many photons would be rejected, the present invention makes it possible to use many additional photons to produce a better signal.

As mentioned earlier, the method according to the present invention can also be used when the stimulation light is irradiated continuously, namely according to the so-called CW STED method. Here, it is important that stimulation light be delivered to the sample already during the pulse of the excitation light. In this phase, all photons coming from the sample are rejected as long as excitation light is irradiated. Upon or shortly after the end of the excitation pulse, the photons coming from the sample are detected and analyzed.

In the case of the CW STED method, the period in which no photons are detected extends beyond the period in which excitation light is irradiated until a certain period after the end of the excitation pulse. In this way, those molecules which are not excited until at the end of the excitation pulse can also be used for a long time because they "see" the stimulation light long enough.

The teaching of the present invention may be advantageously embodied and refined in various ways. In this regard, reference is made, on the one hand, to the claims that are subordinate to claim 1 and, on the other hand, to the following description of the prior art and of two preferred exemplary embodiments of the present invention which make reference to the drawings. In conjunction with the explanation of the preferred exemplary embodiments of the invention with reference to the drawings, an explanation is also given of generally preferred embodiments and refinements of the teaching.

DETAILED DESCRIPTION OF THE PREFERRED EMBODIMENTS

Figure 1:
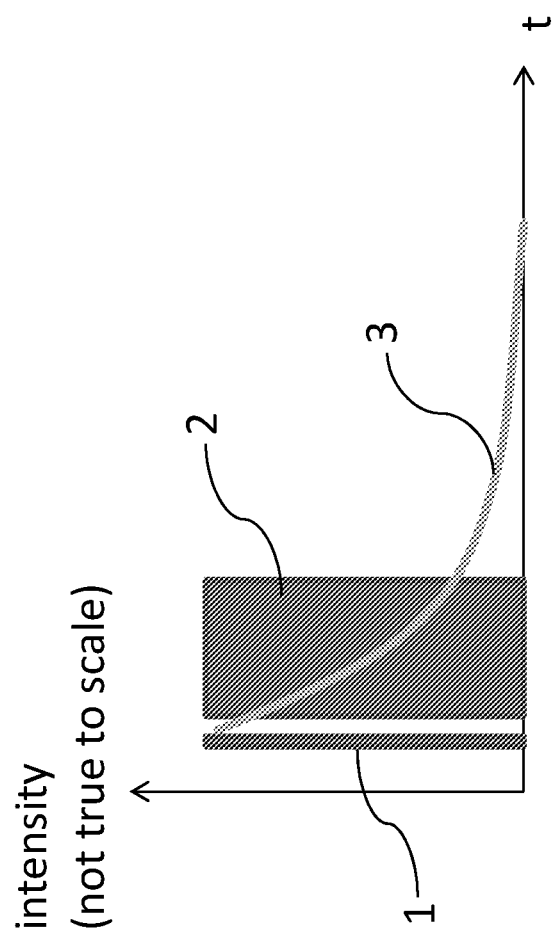
FIG. 1 is a diagram schematically illustrating the intensity time profiles of the excitation light pulse and the stimulation light pulse in the pulsed STED method according to the prior art.

FIG. 1 shows in a simplified diagram the pulsed STED method known from the prior art, and specifically the time profiles of excitation light pulse 1 and STED pulse (stimulation light pulse) 2.

As for excitation light pulse 1, it is essential that it be short compared to the lifetime of the excited state of the dye molecules. If this pulse were longer, then stimulation light pulse 2 pulse would be too late for those molecules which are already excited at the beginning of the excitation light pulse. Such molecules would then emit light before their fluorescence is suppressed by stimulation light pulse 2, which would result in poor resolution.

The curve denoted by reference numeral 3 shows the fluorescence decay that would occur if no stimulation light were irradiated.

Figure 2:
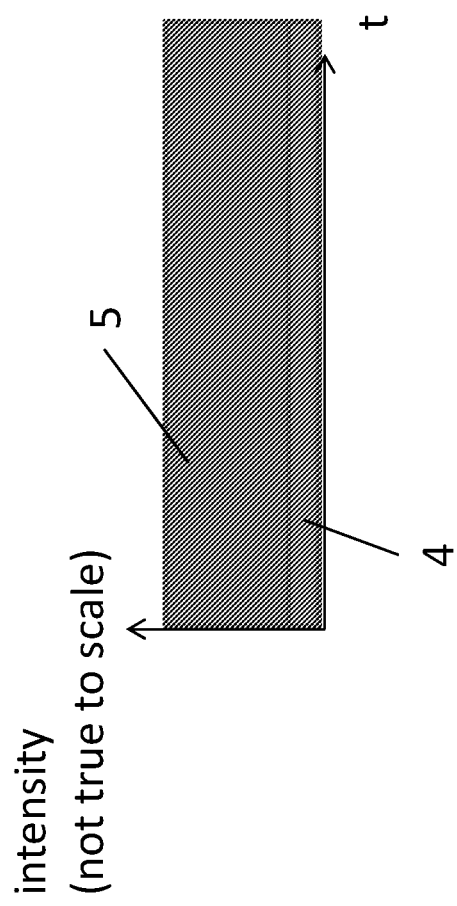
FIG. 2 is a diagram schematically illustrating the intensity time profiles of the excitation light and the stimulation light in the CW STED method according to the prior art.

The diagram of FIG. 2 shows another prior art variant, namely the CW STED method. Here, neither excitation light 4 nor stimulation light 5 (STED light) is pulsed. Rather, here excitation is performed continuously; i.e., the light is irradiated continuously.

Figure 3:
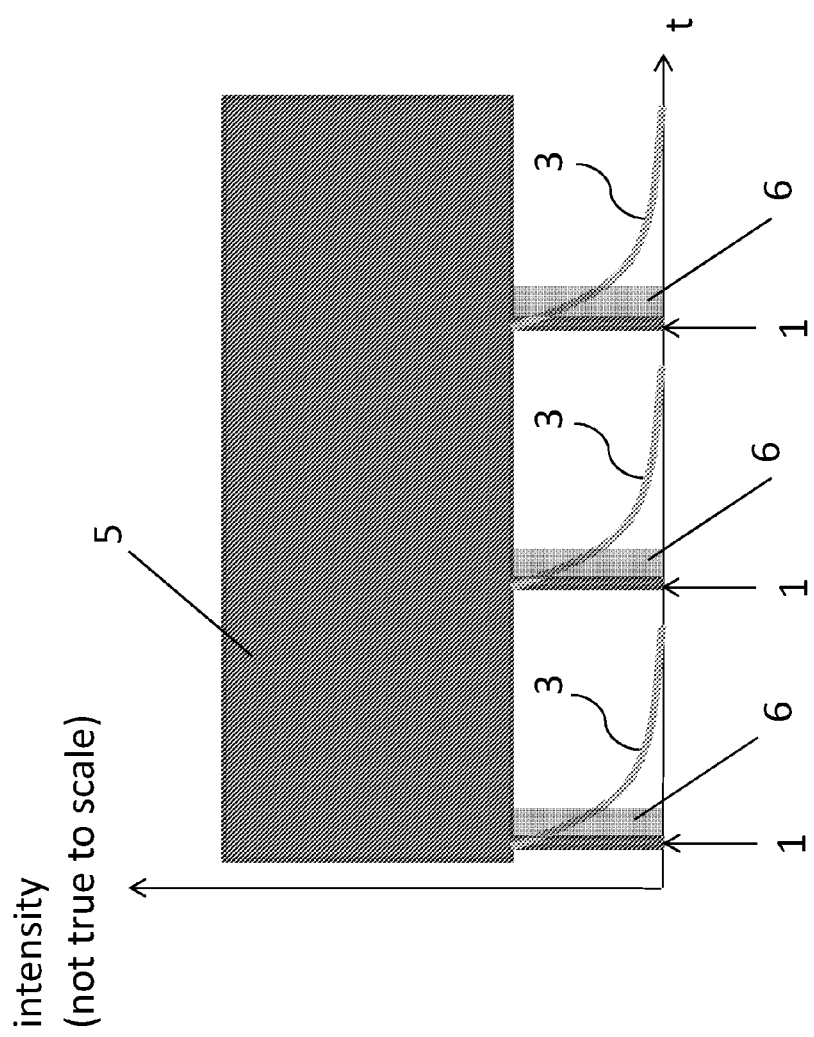
FIG. 3 is a diagram schematically illustrating the intensity time profiles of excitation light pulses and the stimulation light in the gated STED method according to the prior art.

The diagram of FIG. 3 illustrates the so-called gated STED method according to the prior art. Here, stimulation light 5 is irradiated continuously, whereas excitation light 4 is irradiated in short pulses referred to as excitation light pulses 1. Reference numeral 6 denotes the respective rejected periods; i.e., the rejected photons. Curve 3 shows the fluorescence decay that would occur if no stimulation light were irradiated.

Figure 4:
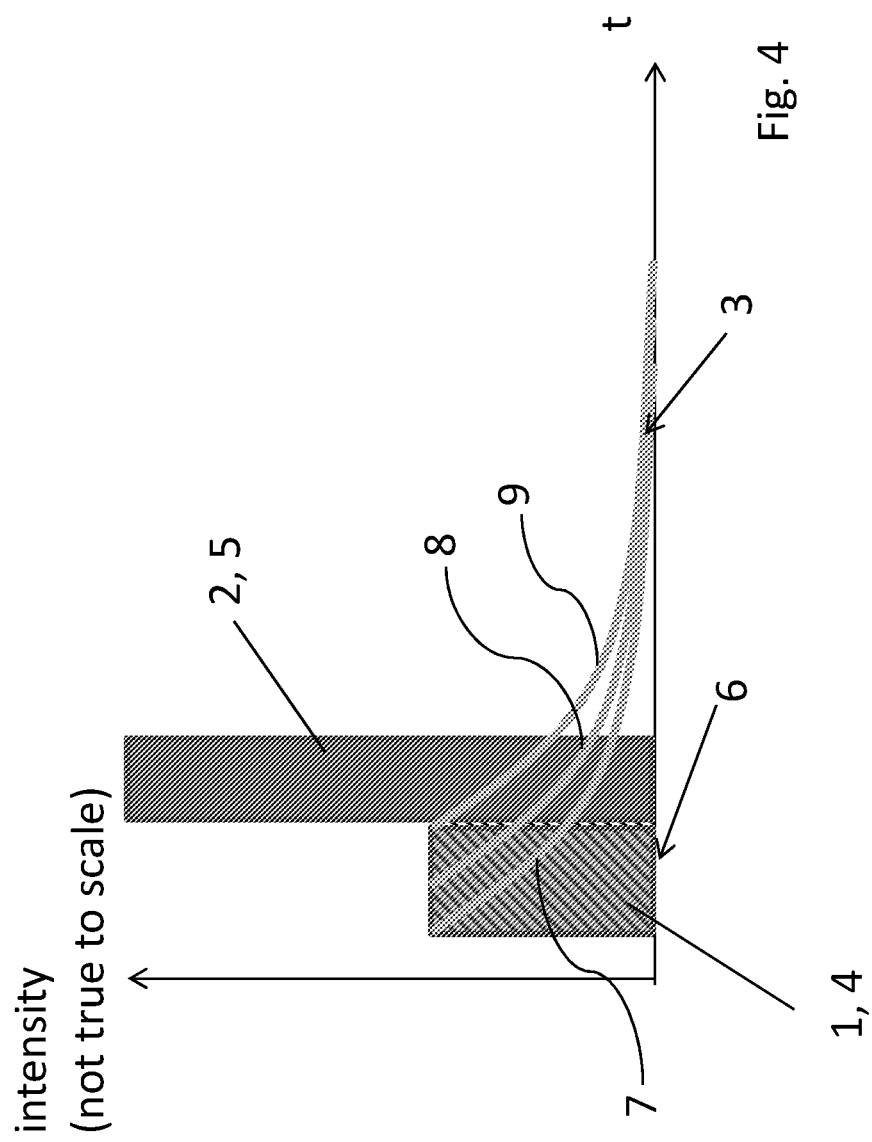
FIG. 4 is a diagram schematically illustrating the intensity time profiles of the excitation light pulse and the stimulation light pulse for the case where the method of the present invention is used in the pulsed STED method with pulsed excitation light and pulsed stimulation light.

The diagram of FIG. 4 illustrates the relationships for pulsed stimulation light 5 according to the present invention.

In contrast to the prior art illustrated in FIG. 1, excitation light 4 is irradiated in a longer excitation light pulse 1 which corresponds approximately to the half of the lifetime of the excited fluorescent state. Since the system shown in FIG. 4 is a pulsed system, no stimulation light or STED light 5 is active at the point in time when excitation light 4 is activated. All photons which are irradiated during the excitation period are rejected as indicated by hatched area 6. They fall within the rejected "gating period". This is because these photons come from the entire excitation region, and not only from the center of the excitation light spot. It is only when stimulation light pulse 2 is active, or shortly after the activation of stimulation light pulse 2, that gating period 6 is deactivated and photons can be detected. These photons are then very likely to come exclusively from the center of the excitation light distribution, as desired.

It is an advantage over the prior art that excitation light 4 or excitation light pulse 1 can be generated using a long-pulse excitation light source, which is inexpensive because of its very simple control electronics and the possibility of using cost-effective laser sources.

Another advantage over the prior art shown in FIG. 1 resides in the fact that the excitation period is longer and, therefore, more photons reach the detector than is possible in the prior art. Since excitation light pulse 1 may correspond to the half of the lifetime [sic] of the excited state of the dye molecule, a significant number of molecules which are excited even at the very beginning of the excitation light pulse will still emit photons after the end of the gating period 6. This is illustrated by curve 7, which represents the probability of emission of photons from molecules which are excited at the beginning of excitation light pulse 1. A large number of them are not emitted until after the end of gating period 6, so that they are also detected. An even greater number of photons can be detected from molecules which are excited in the central portion of excitation light pulse 1. This is illustrated by curve 8. Curve 9 represents the emission period of the dye molecules that are not excited until at the very end of excitation light pulse 1. This corresponds to all molecules that would be excited in the prior art. Accordingly, the prior art rejects many photons which could be used for a better signal, such as taught by the present invention.

Figure 5:
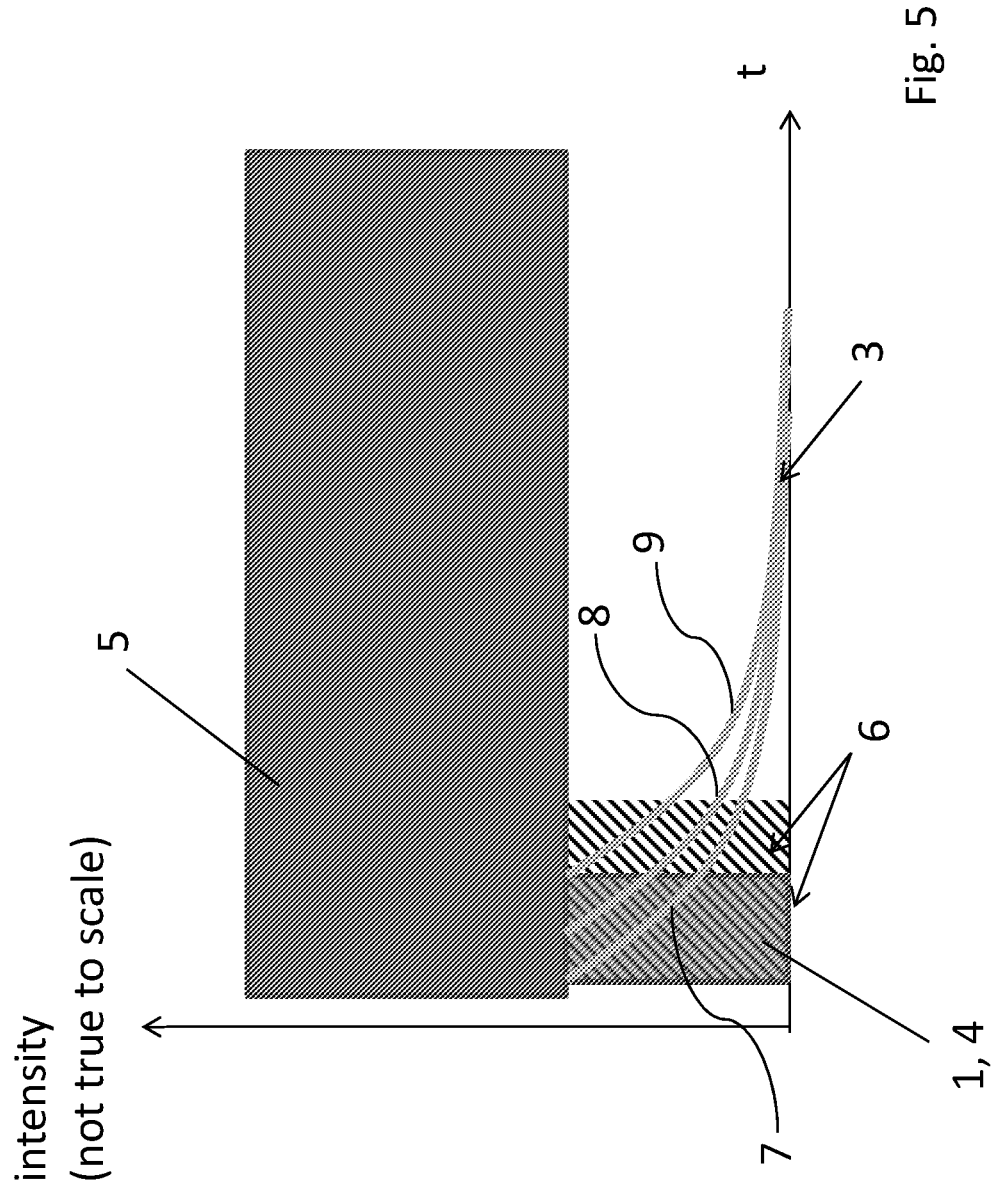
FIG. 5 is a diagram schematically illustrating the intensity time profiles of the excitation light pulse and the stimulation light for the case where the method of the present invention is used in the CW STED method with pulsed excitation light and continuous stimulation light.

The diagram of FIG. 5 shows another exemplary embodiment of the inventive method which is used for the CW STED method. Here, the excitation light is pulsed, such as in the exemplary embodiment of FIG. 4. The STED light or stimulation light 5 is irradiated continuously.

Curves 7, 8 and 9 show the fluorescence decay that would occur if no stimulation light were irradiated.

In FIG. 5, too, the hatched area represents a rejected period 6 in which no photons are detected. This period extends beyond the period in which excitation light 4 is irradiated until a certain period after the end of excitation light pulse 1. This is necessary because the molecules that are not excited until at the end of the excitation light pulse must also "see" the STED light or stimulation light 5 long enough.

It should be particularly noted once again that both the method and the apparatus according to present invention relate to RESOLFT microscopy in general, regardless of the particular method to be subsumed under the term "RESOLFT". What is important here is that the methods are light microscopic methods in which the resolution limit is overcome, namely using photo-optically switchable or controllable states of dye molecules.

With regard to further advantageous embodiments of the method and apparatus according to the present invention, and to avoid repetition, reference is made to the general part of the description and to the appended claims.

Finally, it should be particularly noted that the above-described exemplary embodiments are merely intended to illustrate the claimed teaching, but not to limit it to such embodiments.

LIST OF REFERENCE NUMERALS

1 excitation light pulse
2 stimulation light pulse, STED pulse
3 curve
4 excitation light
5 switching light
6 rejected period, gating period, hatched area
7 curve
8 curve
9 curve

What is claimed is:

1. A Reversible Saturable Optical Fluorescence Transitions (RESOLFT) microscopy method comprising:
   generating excitation light irradiated in light pulses of an illumination pattern of an excitation beam for a sample, using a first pulsed light source;
   exciting a dye molecule within the sample to emit photons of emitted light in response to the excitation light;
   generating switching light, using a second pulsed light source or a continuous light source to switch the dye molecule within the sample between at least two states; and
   detecting the photons coming from the emitted light of the sample by way of applying at least one of optical filtering and temporal filtering,
   wherein the first pulsed light source generates the excitation light with a pulse duration being longer than 150 picoseconds and shorter than a lifetime of an excited state of the dye molecule or shorter than 10 nanoseconds,
   wherein in response to the switching light being irradiated in pulses from the second pulsed light source, no switching light is delivered to the sample during a light pulse of the excitation light and, during the light pulse of the excitation light, the photons emitted from the sample are rejected from detection and analysis, and upon or shortly after activation of a stimulation pulse, the photons emitted from the sample are detected and analyzed, or
   wherein the switching light is irradiated continuously from the continuous light source, the stimulation pulse is delivered to the sample during the light pulse of the excitation light and, during the light pulse of the excitation light, the photons emitted from the sample are rejected as long as excitation light is irradiated, and upon or shortly after an end of the light pulse of the excitation light, the photons emitted from the sample are detected and analyzed.

2. The method as recited in claim 1, wherein the light pulses of the excitation light have a pulse length ranging from 400 picoseconds to 10 nanoseconds.

3. The method as recited in claim 1, wherein the pulse length of the excitation light corresponds approximately to a half-life of a fluorescent state of the dye molecule in the sample that is excited to emission by the excitation light.

4. A method as recited in claim 1, the method further comprising:
   irradiating the sample with pulsed switching light; and
   rejecting the photons emitted from the sample from detection and analysis when no switching light is delivered to the sample during a light pulse of the excitation pulse;
   wherein the step of detecting the photons emitted from the sample by way of applying at least one of optical filtering and temporal filtering further comprises detecting and analyzing the photons coming from the sample after activation of the stimulation pulse.

5. The method as recited in claim 4, wherein the light pulse of the excitation light precedes light pulses of the switching light in time.

6. The method as recited in claim 5, wherein the light pulse of the excitation light comprises an asymmetric time profile, and a falling edge of a light pulse intensity is steeper than a rising edge of the light pulse intensity.

7. The method as recited in claim 5, wherein the light pulses of the switching light comprise an asymmetric time profile, and a rising edge of a light pulse intensity is steeper than a falling edge of the light pulse intensity.

8. The method as recited in claim 1, wherein a light pulse of the switching light precedes the light pulses of the excitation light in time.

9. The method as recited in claim 8, wherein the light pulse of the switching light comprises an asymmetric time profile wherein a rising edge of light pulse intensity is steeper than a falling edge of the light pulse intensity.

10. The method as recited in claim 8, wherein the light pulses of the excitation light comprise an asymmetric time profile and an intensity with a steep falling edge and without a sharply rising edge.

11. A method as recited in claim 1, further comprising:
irradiating the switching light continuously by the continuous light source and delivering the switching light to the sample during a light pulse of the excitation light; and
rejecting the photons emitted from the sample in response to the excitation light for detection as long as the excitation light is irradiated;
wherein the step of detecting the photons emitted from the sample by way of applying at least one of optical filtering and temporal filtering further comprises detecting and analyzing photons coming from the sample after an end of the light pulse of the excitation light.

12. The method of claim 1, wherein RESOLFT microscopy comprises Stimulated Emission Depletion (STED) microscopy, Ground State Depletion (GSD) microscopy, Saturated Pattern Excitation Microscopy (SPEM), Saturated Structured Illumination Microscopy (SSIM) and upconversion microscopy.

13. The method of claim 1, further comprising:
providing a detection beam of photons emitted from the sample along a detection beam path of a scanning microscope; and
filtering the detection beam by an optical filter positioned along the detection beam path to remove switching light reflected from the dye molecule, and portions of the excitation light located outside of the illumination pattern of the excitation beam.

* * * * *